(12) United States Patent
Burnett et al.

(10) Patent No.: US 6,701,185 B2
(45) Date of Patent: Mar. 2, 2004

(54) METHOD AND APPARATUS FOR ELECTROMAGNETIC STIMULATION OF NERVE, MUSCLE, AND BODY TISSUES

(76) Inventors: Daniel Burnett, 12565 Long Lake Ct., Jacksonville, FL (US) 32225; Shane Mangrum, 3701 Danforth Dr. #908, Jacksonville, FL (US) 32224

( * ) Notice: Subject to any disclaimer, the term of this patent is extended or adjusted under 35 U.S.C. 154(b) by 74 days.

(21) Appl. No.: 10/077,434

(22) Filed: Feb. 19, 2002

(65) Prior Publication Data
US 2003/0158583 A1 Aug. 21, 2003

(51) Int. Cl.[7] .................................................. A61N 1/00
(52) U.S. Cl. ............................ 607/2; 607/149; 607/155
(58) Field of Search ................................. 600/9, 13–15; 607/2, 48, 50, 149, 155

(56) References Cited

U.S. PATENT DOCUMENTS

| | | |
|---|---|---|
| 4,428,366 A | 1/1984 | Findl |
| 4,456,012 A | 6/1984 | Lattin |
| 4,548,208 A | 10/1985 | Niemi |
| 5,000,178 A | 3/1991 | Griffith |
| 5,014,699 A | 5/1991 | Pollack |
| 5,181,902 A | 1/1993 | Erickson |
| 5,314,401 A | 5/1994 | Tepper |
| 5,401,233 A | 3/1995 | Erickson |
| 5,518,495 A | 5/1996 | Kolt |
| 5,766,124 A | 6/1998 | Polson |
| 5,792,187 A | 8/1998 | Adams |
| 5,857,957 A | 1/1999 | Lin |
| 6,024,691 A | 2/2000 | Tepper |
| 6,029,090 A | 2/2000 | Herbst |
| 6,032,677 A | 3/2000 | Blechman |
| 6,066,084 A | 5/2000 | Edrich |
| 6,086,525 A | 7/2000 | Davey |
| 6,123,658 A | 9/2000 | Schweighofer |
| 6,143,035 A | 11/2000 | McDowell |
| 6,155,966 A | 12/2000 | Parker |
| 6,179,770 B1 | 1/2001 | Mould |
| 6,190,893 B1 | 2/2001 | Shastri |
| 6,200,259 B1 | 3/2001 | March |
| 6,261,221 B1 * | 7/2001 | Tepper et al. .................. 600/14 |
| 6,349,233 B1 | 2/2002 | Adams |

OTHER PUBLICATIONS

Trock, David H., et al, The Effect of Pulsed Electromagnetic Fields in the Treatment of Osteoarthritis of the Knee and Cervical Spine. Report of Randomized, Double Blind, Placebo Controlled Trials, The Journal of Rheumatology, 1994, p. 1903–1911.

Trock, David H., ELectromagnetic Fields and Magnets Investigational Treatment for Musculoskeletal Disorders, Rheumatic Diseases Clinics of North America, Feb. 2000, vol. 26, No. 1.

(List continued on next page.)

Primary Examiner—Mark Bockelman
(74) Attorney, Agent, or Firm—Maine & Asmus (57) ABSTRACT

An electromagnetic stimulation device which is comprised of a plurality of overlapping coils which are able to be independently energized in a predetermined sequence such that each coil will generate its own independent electromagnetic field and significantly increase the adjacent field. The coils are co-planar and are disposed in an ergonomic body wrap, which is properly marked to permit an unskilled patient to locate the body wrap, on a particular part of the body, of the patient so that the stimulation coils will maximize the electromagnetic stimulation on the selected nerves, muscles, and/or body tissues near the treated area. The device can be used to treat medical conditions including: muscular atrophy, neuropathic bladder and bowel, musculoskeletal pain, arthritis, as well as possible future applications in the prevention of deep vein thrombosis and weight reduction.

10 Claims, 3 Drawing Sheets

OTHER PUBLICATIONS

Shafik, Ahmed, Magnetic Stimulation: A Novel Method for Inducing Evacuation of the Neuropathic Rectum and Urinary Bladder in a Canine Model, Urology 54, 1999, pp. 368–372.

Balmaseda, Marion T. Jr., et al, Burns in Functional Electric Stimulation: Two Case Reports, Archives of Physical Medicine and Rehabilitation, Jul. 1987, pp. 452–453, vol. 38.

McFarlane, J.P. et al, Acute Suppression of Idiopathic Detrusor Instability with Magnetic Stimulation of the Sacral Nerve Roots, British Journal of Urology, 1997, pp. 734–741, vol. 80.

Jacobson, Jerry I. et al, Low–Amplitude, Extremely Low Frequency Magnetic Fields for the Treatment of Osteoarthritic Knees: A Double–Blind Clinical Study, Alternative Therapies, Sept./Oct. 2001, pp. 54–64, vol. 7, No. 5.

EBI, L.P., EBI BONE HEALING SYSTEM, http://www.e-bimedical.com/products/fracture/bonehealing.html, 5 pages.

Certified Pulsed Signal Therapy Centers, http://www.certifiedpst.com, 10 pages.

* cited by examiner

METHOD AND APPARATUS FOR ELECTROMAGNETIC STIMULATION OF NERVE, MUSCLE, AND BODY TISSUES

FIELD OF THE INVENTION

The present invention relates to the field of medical devices, in particular electromagnetic stimulating devices for stimulation of nerve, muscle, and/or other body tissues with applications in the field of medicine.

SUMMARY OF THE INVENTION

The instant invention is drawn to an electromagnetic stimulating device able to provide stimulation to tissues of the human body, including nerves, muscles (including superficial and deep muscles), and/or other body tissues without significant discomfort to the patient. This electromagnetic stimulating device utilizes a plurality of overlapping planar coils encased in an ergonomic, body-contoured wrap. The design of the wrap is intended to allow for ease of use and also for the targeting of anatomic regions to be exposed to the impulses of the electromagnetic fields.

The device of the present invention provides an electromagnetic field to stimulate underlying body tissues in a manner necessary for the several applications including: the prevention/treatment of muscular atrophy, the treatment of neurogenic bladder and bowel, the treatment of musculoskeletal pain, the treatment of arthritis, and/or muscular augmentation. The plurality of overlapping coils are placed in an ergonomic wrap so as to blanket the designated therapeutic area, and thereby provide consistent therapy that can be quickly and easily administered. The invention is designed to be patient user friendly as well as to be portable. It can be used in a hospital, an outpatient clinic, a therapists office, or even at a patient's home.

It is an object of the present invention to provide an electromagnetic device for stimulating regions of the body, which has overlapping coils which can be fired sequentially or in unison depending on the particular required treatment conditions requiring both maximal stimulation (sufficient to cause contraction of muscle fibers) as well as submaximal stimulation (which will be sufficient to provide therapy but not to cause contraction of muscle fibers). The applications of the device can be divided into maximal and submaximal categories, in which the former requires significantly higher levels of inducting current than the latter. The maximal applications of the device include: one, non-invasive stimulation of the peripheral nervous system; two, treatment and/or prevention of atrophy (as would be therapeutic during recovery after a persons sustains a fracture, experiences paralysis of a limb or other body part, or undergoes surgery, such as ACL repair in the knee; and three, treatment of neurogenic bladder and bowel. Submaximal applications of the device include: one, treatment of musculoskeletal pain (e.g. back and neck pain, muscle spasms, and other forms of muscle or skeletal related pain); and two, treatment of arthritis.

It is an object of the invention to provide a device for the electromagnetic stimulation of selective anatomic regions of the body, utilizing an ergonomic wrap to facilitate accurate and targeted placement of the device for the stimulation of key nerves, muscles, and/or body tissues.

It is an object of the invention to provide a device to electromagnetically stimulate selective nerves muscles, and/or body tissues that is user friendly and capable of being used even by an unskilled patient in a home healthcare setting.

It is an object of the invention to provide a device to electromagnetically stimulate selective nerves, muscles, and body tissues to provide consistent therapy, with the ergonomic wrap targeting key nerves and eliminating the requirement for a highly trained operator to manipulate the device.

BACKGROUND OF THE INVENTION AND DESCRIPTION OF THE PRIOR ART

The concept of pulsed electromagnetic stimulation was first observed by the renowned scientist Michael Faraday in 1831. Faraday was able to demonstrate that time varying, or pulsed electromagnetic fields have the potential to induce current in a conductive object. Faraday's experimental setup was simple. He found that by passing strong electric current through a coil of wire he was able to produce pulsed electromagnetic stimuli. This pulsed electromagnetic stimulus was able to induce the flow of current in a nearby electrically conductive body.

In the years since the discoveries of Faraday, pulsed electromagnetic stimulators have found application in countless areas of scientific investigation. In 1965, the scientists Bickford and Freming demonstrated the use of electromagnetic stimulation to induce conduction within nerves of the face. Later, in 1982 Polson et al., U.S. Pat. No. 5,766,124 produced a device capable of stimulating peripheral nerves of the body. This device was able to stimulate peripheral nerves of the body sufficiently to cause muscle activity, recording the first evoked potentials from electromagnetic stimulation.

The ability of pulsed electromagnetic stimulation to induce electrical currents within tissues of the human body has prompted medical research in recent years with respect to the diagnosis, monitoring, and therapy of a variety of important conditions.

Electrical stimulation is a related technology that has been employed for man of years in the treatment of numerous medical conditions. One of the most commonly used for of electrical stimulation takes the form of what is known as TENS (Transcutaneous Electrical Nerve Stimulation) unit. These devices are designed specifically to stimulate nerve tissue that will block or interrupt pain signals being sent to the brain.

This class of electrical stimulating devices utilizes the principles of direct nerve stimulation to excite nerves. These technologies place electrodes directly on the skin or on occasions beneath the skin in a surgically implanted fashion. The electrodes carry wires, through which electrons flow and create a transfer of charge to the tissues and nerve cells beneath.

Electrical stimulation can be effective in stimulating superficial tissues, as stimulation is usually accomplished from small electrodes, with moderate voltage and current levels. Electrical stimulation, however, can cause significant skin irritation and burns as has been reported in a significant number of cases within the medical literature (Balmmaseda M T, et al. Burns in functional electric stimulation. Archives of Physical Medicine and Rehabilitation. July 1987; 68(7) 452–53). In its alternative forms, such as with surgically implanted electrodes, electrical stimulation can be invasive and consequently associated with adverse side effects. The difficulties with electrical stimulation become especially significant as large excitation levels are required for more complete stimulation of nerves.

The limitations of electrical stimulation have prompted investigations into the possible applications of pulsed electromagnetic stimulation. The basic principal behind the concept of electromagnetic stimulation is that an electric current pulsed, or passed through a coil winding structure will generate an electromagnetic field. An electromagnetic field can, in turn, generate a current in any conductive material, such as nerves or other body tissues, within this field.

The electromagnetically induced electric field created by properly oriented pulsed electromagnetic stimulation thus accomplishes the result of transferring charge to cells of the body. This transferred charge can lead to nerve firing, muscle contraction, stimulation of cell signaling pathways causing cell growth, and a number of other effects.

In contrast to applications of electrical stimulation, pulsed electromagnetic stimulation does not require direct skin contact to induce nerve excitation. As a result, significantly higher levels of directed stimulation can be achieved though pulsed electromagnetic stimulation without the adverse effects of other technologies.

The ability of electromagnetic stimulation to induce electrical currents within tissues of the human body has prompted medical research in recent years with respect to the diagnosis, monitoring, and therapy of a variety of conditions, including: preventing and treating muscle atrophy, treating neurogenic bowel and bladder, offering pain control for musculoskeletal and back pain, and treating arthritis.

The device of the present invention is a powerful electromagnetic stimulating device created for the purpose of stimulating nerve, muscle, and/or other body tissues. The device builds on existing electromagnetic stimulator technology to provide an easy-to-use, ergonomically designed system that will have applications within a host of clinical and home ease of use health applications.

One of the earliest applications of electromagnetic stimulating technology took the form of bone growth stimulators. These devices employ low frequency pulsed electromagnetic fields to stimulate bone repair. Bone growth stimulators first found use approximately 20 years ago in the treatment of non-healing fractures, and are slowly becoming the standard of care for this condition.

As investigators have studied the effects of electromagnetic fields on fracture healing, it has been demonstrated that low frequency pulsed electromagnetic fields can not only facilitate fracture healing but also cause the growth of cartilage cells (Rheumatic Diseases Clinics of North America, 26(1):51–63, February 2000). This ability to stimulate new cartilage growth creates a tremendous potential for treating arthritis.

The effects electromagnetic fields on the repair of cartilage and soft fibrous tissues have been demonstrated in a number of recent studies. Pulsed electromagnetic devices have been shown to be effective in treating patients with chronic knee arthritis, demonstrating that this treatment effective in the reducing pain and improving function. (Rheumatic Diseases of Clinics of North America, 26(1) 52–63, February 2000).

Not only has electromagnetic stimulation been shown to improve repair of cartilage and soft tissues, it has also been shown to be safe and cost-effective for treating patients with chronic knee pain due to arthritis (Altern Ther Health Med, 7(5):54–64, September–October 2001). The treatment has not been demonstrated to have any side effects and may be useful in forestalling joint replacements.

The present invention also provides a simple, noninvasive solution to the problem of neuropathic bladder and rectum, such as persons with spinal cord injuries or Multiple Sclerosis might experience. Just as these persons may have paralysis of the arms or legs, they can also have a so-called "paralysis" of the bladder and bowel, with associated difficulty emptying the bladder and bowels. Complications that can arise from neurogenic bladder and bowel are significant. In mortality studies of persons with spinal cord injuries, after a period of high mortality at the time surrounding the initial injury, neurogenic bladder has been shown to be the primary cause of death among persons with spinal cord injuries.

Invasive methods have been attempted to address this problem but without significant success. In animal models electromagnetic stimulation has been shown to increase bladder and bowel pressures, and to thereby effect evacuation (Urology, 54(2) 368–72, August 1999). This technique is simple, safe, noninvasive, and has no known adverse effects.

The present invention also provides a treatment for one of the major causes of stress urinary incontinence—a condition referred to as 'idiopathic detrusor instability.' Detrusor instability describes the unstable contractions of the detrusor muscle (a muscle controlling the release of urine from the bladder), which can cause persons to lose, or be incontinent of urine. Studies have shown that electromagnetic stimulation of sacral (an area of the lower spine) nerve roots acutely abolishes unstable contractions in patients with this condition (British Journal of Urology, 80(5):734–41, November 1997).

The prior art devices provide electromagnetic stimulators, which utilize pulse electromagnetic fields to promote positive effects on the human body. These effects have been well-established in multiple large, double-blind, placebo-controlled studies in the medical literature. The device of the present invention substantially improves the state-of-the-art electromagnetic stimulation technology and incorporates it into a user-friendly, body-contoured applicator with multiple overlapping coils to effectively carpet the entire targeted subcutaneous region.

Considered as a group, existing electromagnetic stimulators cannot be operated by the patient but require a skilled technician. These devices employ a single, focused coil of varying configurations to provide electromagnetic induction. While this may be practical for diagnostic purposes, it is not user friendly or cost-effective for the treatment of muscle atrophy, neurogenic bladder and bowel, musculoskeletal pain, arthritis, and a host of other conditions.

There have been limited attempts in the prior art to solve the existing problems associated with the use of electromagnetic stimulation devices. One such example of electromagnetic stimulation is described in U.S. Pat. No. 6,086,525 issued to Davey et al. Davey discloses a device that has a single coil in the shape of a "C" where the intensity of the electromagnetic field is between the ends of the "C". That point must be employed directly over the target nerve or muscle to be stimulated. The coil is toroidal in configuration and utilizes a unique core of vanadium permendur in the preferred form. One of the disadvantages of this device is that it requires a trained technician to treat the patient and to properly hand hold the open end of the "C" over the targeted nerve or muscle to be stimulated. The device is not portable and is designed for use in hospitals or similar institutions. Also the vanadium permendur core is required to increase the strength of the electromagnetic field to be strong enough to be effectively used. The design, shape and configuration described in Davey and other prior art devices, require the electromagnetic stimulator to be hand operated during use.

Further, Davey is specifically designed to discourage secondary stimulation sites. It is intended to focus and concentrate the field to a single point. However, for therapeutic use the nerves and muscles that need stimulation are not located at a singe point but in a larger area and hence the focus of the field needs to radiate to a larger area and not be isolated to a single point. In fact secondary muscle stimulation is necessary for proper treatment in many applications.

The present invention eliminates the need to have a trained technician conduct the electromagnetic stimulation by providing an ergonomic wrap that encases the overlapping coils. The wrap with reference indica is designed to enable an unskilled patient to properly place the wrap such that the proper key nerves, muscles, and/or other body tissues are stimulated A trained physician will prescribe the planned degree of electromagnetic stimulation required, both in time and intensity.

The use of a solid core is also required in Davey to generated sufficient electromagnetic field intensity to stimulate the nerves, muscles, and/or other body tissues. The Present invention overcomes the need for a solid core by providing overlapping coils that electrically amplify the intensity of the electromagnetic field so as to stimulate the nerves, muscles, and/or other body tissues. Also since no solid core is required in the present invention the overlapping coils can be planar and disposed within a flexible ergonomic body wrap that is not contemplated or possible using the devices of the prior art. The plurality of overlapping coils also provides an appropriate area of intense electromagnetic stimulation to bathe the nerves, muscles, and/or body tissues more thoroughly than any of the existing single coils devices.

The present invention proposed a separate flexible wrap designed for each part of the body to be treated. Each such body wrap has marking indicia that enable an untrained patient to properly locate the stimulation coils to effectively treat that specific area of body. No skilled technician need be used in the treatment. The devices of the prior art cannot be used in a flexible body wrap because of the necessity to utilize a solid single core.

Hence, the device of the present invention permits the planar coils to be used in a flexible body wrap, not contemplated or possible by any prior art device. The overlapping coils create an amplified electromagnetic field to stimulate nerves, muscles, and/or other body tissues without the use of using a solid core. These advancements are not taught or contemplated by the prior art and produce an unexpected increase in the electromagnetic field intensity capable of stimulating nerves, muscles, and/or other body tissues. As such the overlapping coils can be placed in a flat plane (or in a contoured plane surrounding a particular part of the body), or disposed in an ergonomic flexible body wrap also not contemplated by the prior art devices.

DETAILED DESCRIPTION OF THE INVENTION

DRAWINGS

These and other features, aspects and advantages of the present invention would become better understood with reference to the following description, appended claims and the accompanying drawings where:

DETAILED DESCRIPTION OF THE INVENTION

The following is a description of an electromagnetic stimulating device of the present invention that comprises or alternatively consists of a logic controller coupled to an array of coils, disposed within an ergonomic body wrap for use by patients for self-treating the conditions described herein.

Figures 1, 2:
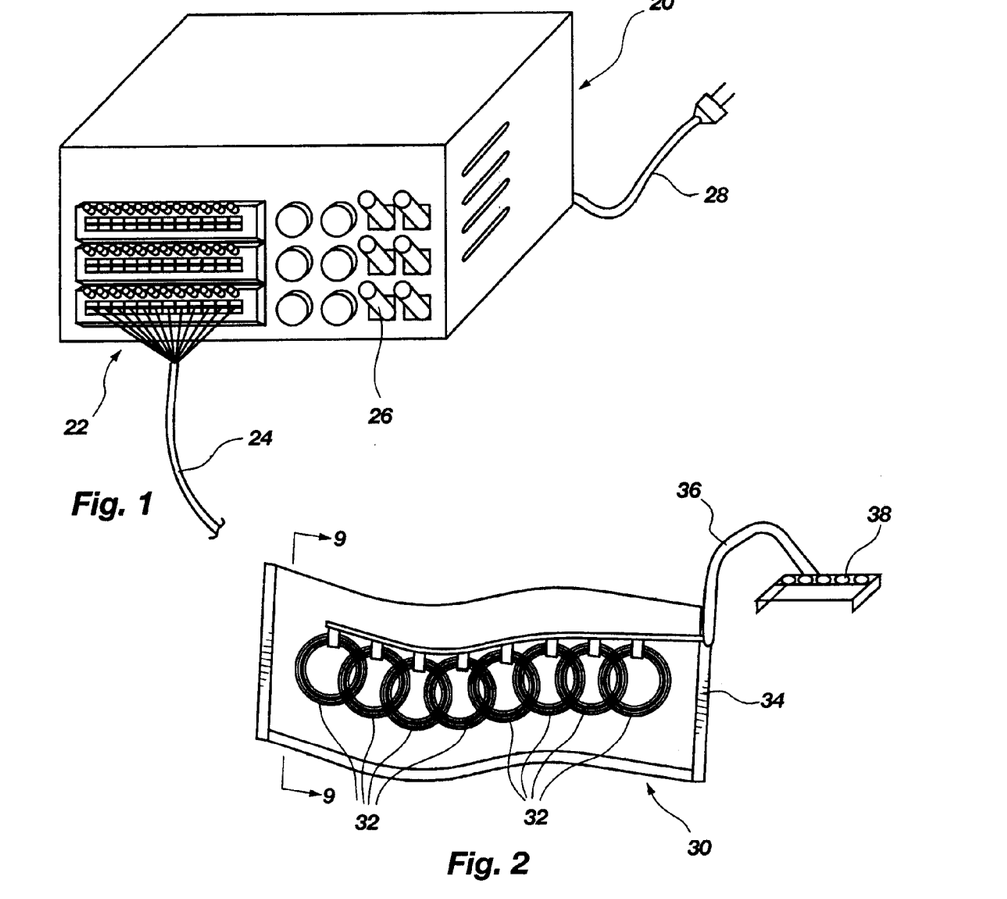
FIG. 1 is an illustration of a logic controller, which can be coupled to an ergonomic wrap containing the overlapping planar coils.
FIG. 2 is a simple ergonomic strap containing the coils of the present invention.

The logic controller 20, FIG. 1, is a device through which current is provided to an array of stimulation coils. The logic controller 20 controls the activation of the stimulation coils, as well as the rate of stimulation of a given coil. The logic controller also allows for the adjustment of stimulatory channels and/or for the amount of current provided to any one coil at any one time. In one embodiment, FIG. 2, a simple ergonomic strap 30 is shown having a positioning locking mechanism like Velcro for holding it in place. The strap 30 has a body 34 into which the planar flexible coils 32 is disposed. One or more arrays of coils 32 can be electrically charged by the logic controller 20 by means of a multiple socketed plug 38, which has a socket and lead for each coil 32 and is coupled to each coil by means of electrical wiring 36. The logic controller 20 permits the activation or deactivation of individual coils, as well as adjustment of the rate of stimulation and the amplitude of the stimulus. Three or more arrays of coils 32 may be controlled by the logic controller 32 for allowing stimulation of multiple coils in sequence or simultaneously.

The logic controller 20 in the preferred embodiment is lightweight and easily transportable. The logic controller 20 preferably plugs into a standard U.S. outlet (115 Volts, 10 Amps, 60 Hz) by means of a standard plug 28, FIG. 1. In alternative embodiments, the logic controller 20 is designed to plug into a standard European outlet, a standard Japanese outlet, a standard Canadian outlet, or a standard Australian outlet. Still in other embodiments, the logic controller 20 plugs into either an AC or a DC outlet.

The logic controller 20 of the present invention is not claimed to have any circuitry that is not well known in the art. However, for explanation purposes the circuitry of the preferred embodiment is described hereinafter without reference to a schematic or drawing.

The internal circuitry of the logic controller 20 comprises or alternatively consists of a transformer, a capacitor, an inducting coil, a diode, and a switch. The logic controller 20 can further comprise or consist of a bridge rectifier.

A transformer (not shown) is a device that takes a first current and voltage and converts it to a second current and voltage through electromagnetic induction. For example transformer (1:2) has an output of approximately 230 Volts and 5 Amps. In some embodiments, the transformer is 1:1 with an output of 115 volts (~170 post bridge-rectifier). In alternative embodiments the transformer as an output of at least 50 volts, at least 100 volts, at least 150 volts, at least 200 volts, at least 250 volts, at least 300 volts, at least 400 volts, or at least 500 volts. In other alternative embodiments the transformer bus an output of at least 1 Amp, at least 2.5 Amps, at least 5 Amps, at least 10 Amps, or at least 20 Amps.

A bridge rectifier (not shown) is for example an electrical component consisting of four diodes that when wired to a transformer will convert AC to DC. The bridge rectifier converts the output voltage from AC to DC. The bridge rectifier must be rated to at least 1 kW and 350 Volts as the rectified output voltage will be approximately 320 Volts. In alternative embodiments, the bridge rectifier is rated to at least 120 volts, at least 250 volts, at least 300 volts, at least 350 volts, or at least 400 volts. In other alternative embodiments, the bridge rectifier is rated to at least 100 W, at least 500 W, at least 2,000 W, at least 5,000 W, or at least 10,000 W.

A capacitor and a stimulating coil (not shown) are provided in parallel. For example the capacitor is at least 40,000 microfarads and is rated to 320 Volts, and provides approximately 2050 Joules/pulse. In alternative embodiments, the capacitor is at least 20,000 microfarads, at least 30,000 microfarads, at least 35,000 microfarads, at least 45,000 microfarads, at least 50,000 microfarads, at least 100,000 microfarads, at least 500,000 microfarads, at least 1,000,000 microfarads, or at least 5,000,000 microfarads. In other alternative embodiments the capacitor is rated to at least 120 volts, at least 200 volts, at least 250 volts, at least 300 volts, at least 350 volts, at least 400 volts, or at least 450 volts.

In yet other preferred embodiments, the capacitor is rated to only 200 Volts at less than 7000 microfarads. In alternative embodiments, the capacitor is rated to no more than 400 volts, no more than 300 volts, no more than 250 volts, no more than 225 volts, no more than 200 volts, no more than 175 volts, no more than 150 volts, no more than 125 volts, or no more than 100 volts. In other embodiments the capacitor is no more than 10,000 microfarads, no more than 9,000 microfarads, no more than 8,000 microfarads, no more than 6,000 microfarads, no more than 5,000 microfarads, or no more than 4,000 microfarads.

The inducting coil FIG. 1, is any overlapping array of coils 32 that is disposed within an ergonomic wrap 30 to cover the tissues for which the stimulation is intended. One or more coils or arrays of coils may be attached to the logic controller as described in more detail below.

Between the capacitor (not shown) and the inducting coil is a diode to prevent ringing and oscillation between the capacitor and inductor. In one form the diode is preferably of the same rating as the bridge rectifier described above.

Distal to the inductor is a switch (not shown) that in one position allows the capacitor to discharge to ground through the stimulating coils 32. In the other position, the switch prevents the capacitor from discharging to ground and allows the capacitor to be charged. Each coil 32 attached to the logic controller 20 may have its own internal switching mechanism to allow firing of the coil 32 in sequence or to allow the firing of multiple coils simultaneously. In preferred embodiments, the switch activates a stimulation repetition rate of at least 1 Hz and a pulse duration of greater than 10 milliseconds. In other preferred embodiments, the pulse duration is greater than 1 milliseconds, greater than 5 milliseconds, greater than 25 milliseconds, greater than 50 milliseconds, greater than 100 milliseconds greater than 125 milliseconds, greater than 150 milliseconds, greater than 175 milliseconds, or greater than 200 milliseconds. In other referred embodiments the stimulation repetition rate is at least 0.5, 10, 25, 50, 100, or 500 Hz.

In preferred embodiments, stimulation occurs through firing each coil 32 individually, while using switches to short out the overlapping coils 32 to prevent low-impedance interference. In the preferred embodiment there is one target coil (the center coil). The two flanking coils are charged as is the target coil (the center coil) in a predetermined sequence. The coil orientation will be such that the fields generated by the coils will be additive with maximum field generation being in the areas between the target and flanking coils. The choice of mode of stimulation will depend on the needs of the site of stimulation and will be programmable using methods and apparati well known in the art.

In a preferred embodiment, the step-up transformer is linked to the bridge rectifier, which is linked in parallel to a capacitor and inducting coil between which is a diode, and wherein the inducting coil is linked to a switch.

The array of coils 32, FIG. 2, may take a variety of configurations. In preferred embodiments, the coils overlap to ensure that the subcutaneous tissue is adequately carpeted, see FIGS. 2 through 8. In preferred embodiments, the coils 32 overlay the tissue for which the stimulation is intended.

In preferred embodiments, each coil will be between 5 and 100 mm in diameter. In alternative embodiments, each coil will be at least 5 mm, at least 10 mm, at least 20 mm, at least 40 mm, at least 75 mm at least 100 mm, at least 125 mm, at least 150 mm, or at least 200 mm in diameter. In preferred embodiments, each coil has a 40 mm diameter.

In preferred embodiments each coil consists of insulated wire, either threaded or single core, for example, wrapped multiple times to obtain a configuration of overlapping circles. Preferably, the coils are #12 insulated flat-wound copper wire wrapped 20 times. In other embodiments the coils are #10, #14, #16, #18, or #20 insulated flat-wound copper wire.

In alternative embodiments, the wire is wrapped 5, 10, 20, 40, 75, 100, or 200 times, for example. Each coil will be its own insulated circuit connected to the logic controller allowing the coils to be stimulated individually or in unison. In other embodiments, all the coils are activated in unison. In preferred embodiments the overlap between adjacent coils is 25%. In other embodiments the coils may overlap 5%, 50%, or 75%.

Figure 9:
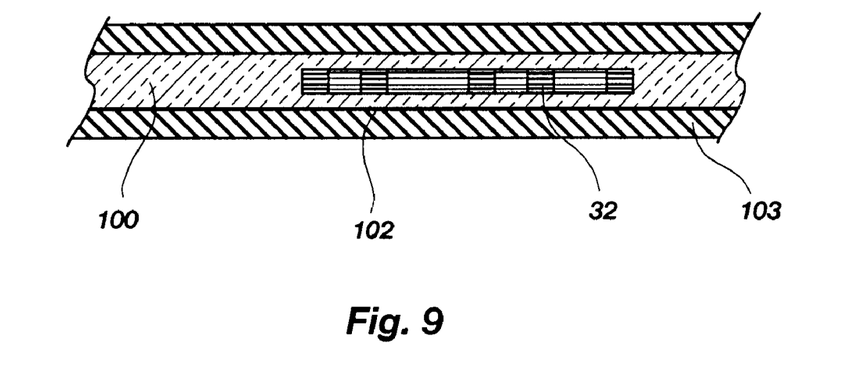
FIG. 9 is a cross-sectional view of a typical ergonomic wrap of the present invention.

In the preferred embodiment, FIG. 9, the entire array of coils 32 is enveloped in a non-conducting material 100 (e.g. plastic, rubber, ceramic), over which is a thin layer of conducting mesh 102 (aluminum, copper, steel, for example) and the last layer of non-conducting material 103 (e.g. plastic, rubber, ceramic) will be laid. Preferably, the last layer of non-conducting material 103 is a comfortable to the skin, but thin cloth allowing non-irritating application to the dermis. The conducting mesh 102 will preferably be placed on both sides of the coils such that the logic controller will be disabled immediately if a short circuit occurs. If any current escapes the coil insulation 32, the conducting mesh 102 will trap the current and blow an internal fuse disabling all current so as to protect the patient and/or caregiver. This safeguard helps to ensure that the patient and/or caregiver is not exposed to a shock from a short circuit.

In preferred embodiments, the coils 32 are then incorporated into a design for ease of application in an ergonomic body wrap. These designs can include, but are not limited to, a shoulder harness 90 FIG. 8, a pelvis wrap 40 FIG. 3, a knee wrap 70 FIGS. 6 & 7, a lumbosacral belt 60 FIG. 5, an elbow applicator (not shown), a thigh wrap 50 FIG. 4, and a simple flat strap 30, FIG. 2. Each design is preferentially ergonomically designed for ease of application and accuracy in targeting key tissues. Other possible designs include, but are not limited to, hand, foot, neck, face, full-body or half body (i.e. both legs) applicator wraps. In preferred embodiments, each design, except for the simple strap, will have coils strategically placed to target and stimulate key tissues. The simple strap 30, FIG. 2, will have coils 32 in a linear fashion throughout its entire length to make it a more flexible applicator. Preferably, the wraps are secured in place with Velcro. However other means of fastening include buckles, snaps, zippers, hooks, etc, may be used. In alternate embodiments no fastening means is used instead the fabric of the wrap is stretchable and able to hold itself in place because of the elasticity. In each body wrap, for example strap 30, each stimulation coil 32 is individually connected to an insulated wire disposed within the distribution line 36 so that it can be connected to plug 38 such that each wire can individually energized when plug 38 is inserted into the logic controller 20, FIG. 1. The logic controller 20 permits selective energization of each coil.

The present invention is intended for use in any situation in which electromagnetic stimulation of tissues is desired. Conditions in which this invention would be indicated include prevention/treatment of atrophy (such as in cancer, AIDS, myositis, paralysis, Guillain-Barre, routine fractures, coma, bedridden patients, etc.), treatment of neurogenic bladder and bowel, treatment of musculoskeletal pain and treatment of arthritis. For each of these indications, scientific evidence exists concerning the benefits of electromagnetic stimulation. Furthermore, the invention could be used as a means of muscular augmentation outside of the medical field by athletes and those desiring increased muscle mass. Alternatively, the invention is useful for the prevention of deep venous thrombosis in bedridden or immobilized patients, and weight reduction.

The device of the present invention can also be used for patients who are in a cast, for example one having a broken leg. The muscles in the leg and cast area will atrophy during the time the cast is in place. Since the present invention does not require direct skin contact the thigh wrap 50 of the strap 30 can be placed under, over, or be incorporated into the cast to stimulate the immobilized muscle(s). The electromagnetic field that is created will stimulate the muscles in the casted area and prevent their atrophy.

For therapeutic use, the invention should be used at least twenty minutes each day for each site of stimulation in two ten minute increments spaced 4–8 hours apart. This is a minimum and these values may be increased as the caregiver (physician or therapist, for example) sees fit for accelerated recovery. Alternative treatments for include 15-minute treatments spaced 20 minutes apart and all increments up to and including 10 minute treatments spaced 24 hours apart. Therapy for muscular atrophy should last at least a week with the upper end being months (or even years) for patients with conditions resulting in long-term immobilization. Therapy for neurogenic bladder/bowel, musculoskeletal pain and arthritis should be administered on an as needed basis ad infinitum.

For applications requiring maximal stimulation (such as in the treatment/prevention of atrophy and the treatment of neurogenic bladder and bowel), the delivered stimulation should result in contraction of muscle fibers as assessed through observation and physical exam. The actual contraction strength, though, may be therapeutic with only induction of twitches. For applications requiring submaximal stimulation (such as the treatment of musculoskeletal pain and arthritis), the stimulation should not result in contraction of muscle fibers.

Figure 3:
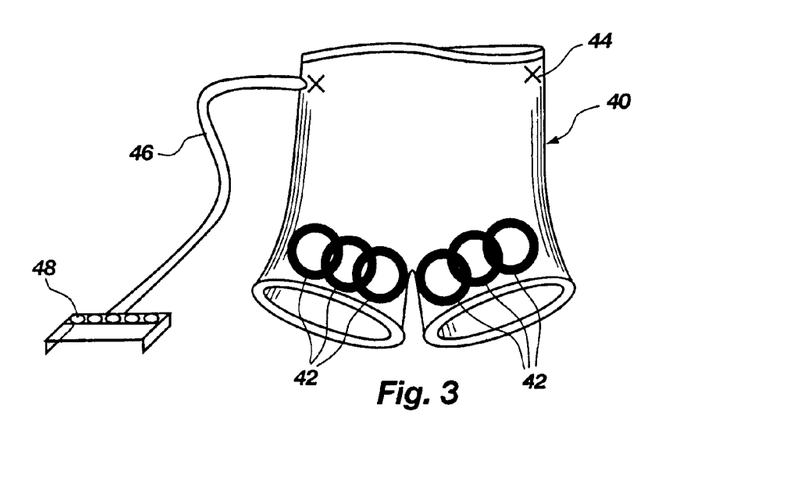
FIG. 3 is an ergonomic pelvic wrap containing the coils of the present invention.
Figures 4, 5:
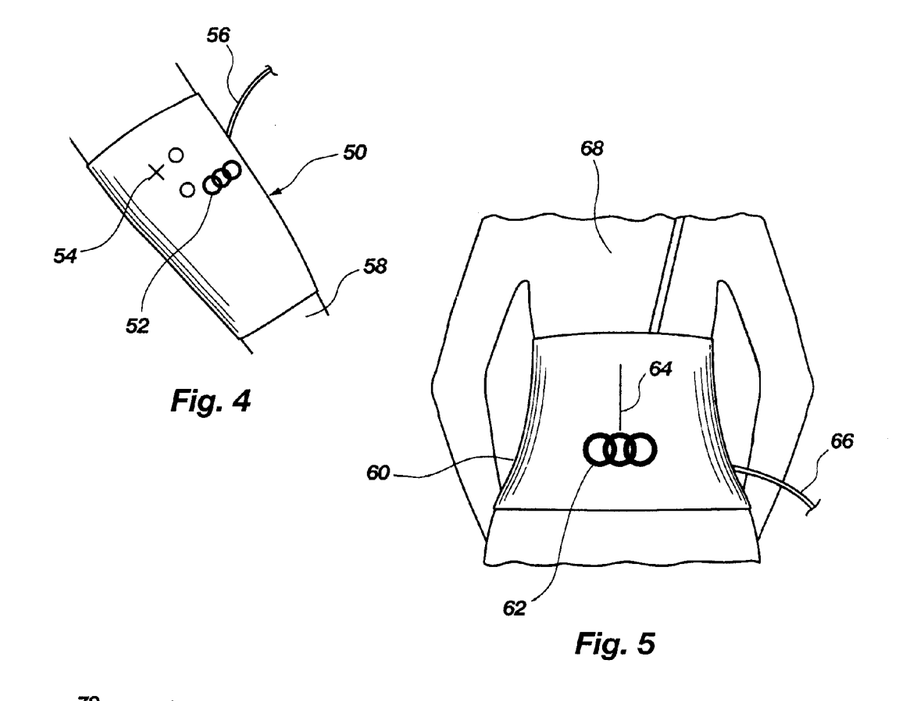
FIG. 4 is an ergonomic thigh wrap containing the coils of the present invention disposed on the thigh of a patient.
FIG. 5 is an ergonomic lumbar/sacral wrap containing the coils of the present invention disposed on the back of a patient.
Figure 6:
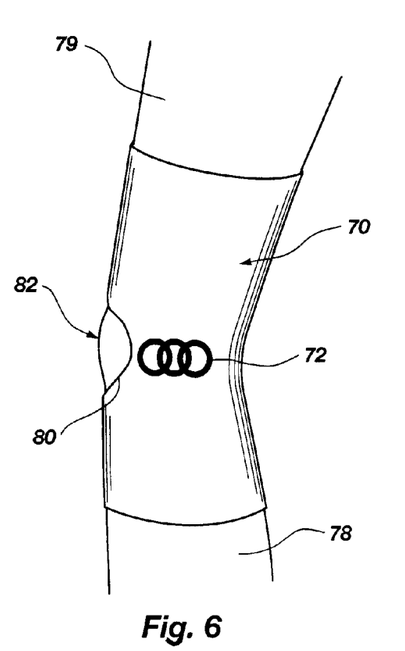
FIG. 6 is a side view of an ergonomic knee wrap containing the coils of the present invention disposed on the knee of a patient.
Figure 7:
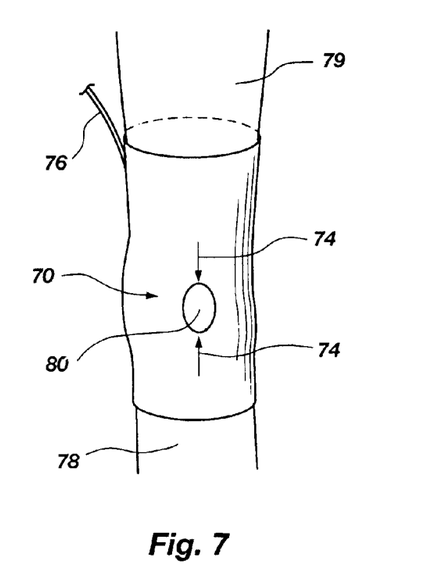
FIG. 7 is a front view of an ergonomic knee wrap containing the coils of the present invention disposed on the knee of a patient; and, FIG. 8 is a front view of an ergonomic shoulder wrap containing the coils of the present invention disposed on the shoulder of a patient.
Figure 8:
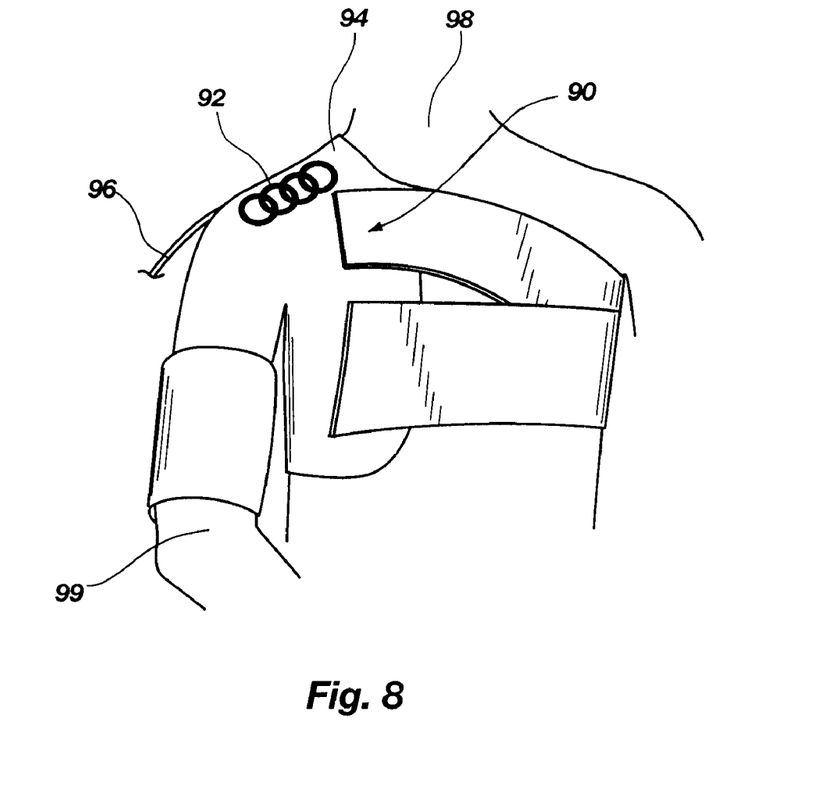

The applicators should be placed in their intended positions, (i.e. elbow wraps on the elbow, not the knee) due to the strategic placement of stimulatory coils 32 in each body wrap. The body wraps are designed such that they fit ergonomically and require little thought or effort in placing them. Each wrap has marking indicia thereon to aid in the proper placement of the body wrap so that the proper nerves, muscles, and/or other body tissues may be stimulated. For example, the marking indicia in the: pelvic wrap 40, FIG. 3, are to be located directly over the sacral and/or lumbar spinal processes 44; in the thigh wrap 50, FIG. 4, are to be placed directly over the greater trochanter of the femur 54; in the knee wrap 70, FIG. 7, are to be located over the middle of the top of the knee cap(patella)74; in the lumbosacral belt 60, FIG. 5, are to be placed over the spinous processes in the midline of the lumbar spine 64; and, in the shoulder sleeve 90, FIG. 8, are to be located over the clavicle bone (collar bone) 94. Alternatively, the device of the invention should be used as the patient and their health care provider see fit.

The overlapping coils 32 are placed in each of the body wraps to identify certain nerves, muscles, and/or other tissues to maximize the effect of the stimulation. The placement of the stimulation coils are shown in each application. In the pelvic wrap 40 FIG. 3, the stimulation coils 42 are disposed anterior and posterior thigh. In the thigh wrap 50, FIG. 4, the stimulation coils 52 are to be located over the anterior and/or posterior thigh. In the shoulder sleeve 90, FIG. 8, the stimulation coils 92 are placed over the area adjacent to the spine of scapula and supraspinatous muscle. In the knee wrap 70, FIG. 6, the stimulation coils 72 are placed over the medial joint (or the space between the femur and tibia). In the lumbosacral belt 60, FIG. 5, the stimulation coils 62 are placed over the sacral and/or lumbar spine.

The following Examples are provided for illustration, not limitation. One with skill in the art would be able to use these examples as guidelines for making and using comparable devices.

EXAMPLE 1

Empirical Testing of Maximal Applications

The optimal stimulus intensity for prevention/treatment of atrophy, treatment of neurogenic bladder and bowel and muscle augmentation; the optimal application parameters, i.e. frequency of stimulation, duration of treatment, location of stimulatory coils in each disposable array of coils; and the optimal coil diameter/placement within the strays can be determined using the following experimental protocol:

Before, during and after treatment, muscle mass will be measured by limb circumference and, in the later stages, muscle biopsy. Contraction strength, and therefore effectiveness of individual impulses, will be measured using electromyography of the involved musculature. In the case of neurogenic bladder and bowel, effectiveness of individual impulses will be assessed with observation of voiding efficacy.

EXAMPLE 2

Empirical Testing of Submaximal Applications

The optimal treatment of musculoskeletal pain and arthritis can be tested by monitoring patient satisfaction and reported relief of symptoms. The optimal pulse amplitude, duration, and site of stimulation will be assessed on an individual basis. Wide-based operating parameters will be determined through clinical testing of the device and subjective patient responses to survey questions.

The preferred embodiment of the present invention has been described in detail herein. The stimulation coils 32 have been described as planar, however the plane that the coils may be disposed in while in use will be in a plane that contours to that particular part of the body. The devices is also described as not having to use a solid core in order to create a magnetic field of sufficient strength because of the over lapping of the stimulation coils 32. However, it is possible in alternative embodiments that a solid core of some kind may be beneficially used while the body wrap is still able to fit and contour the body.

Although the present invention has been described in considerable detail with regard to certain preferred variations thereof, other versions or embodiments are possible. Thus, the spirit and scope of the appended claims should not be limited to the description of the preferred version contained herein.

What is claimed is:

1. An electromagnetic stimulating device comprising a plurality of overlapping stimulator coils for conducting electrical current disposed in an ergonomic flexible body-contoured wrap capable of being adjustably and temporarily secured to the body of a patient in an appropriate orientation by an unskilled user; and an electrical current means connected to said overlapping stimulator coils so as to be able to independently energize each coil in a predetermined sequence such that each coil will generate its own independent electromagnetic field.

2. The electromagnetic stimulating device of claim 1, wherein said overlapping stimulator coils are co-planar.

3. The electromagnetic stimulating device of claim 1, wherein said flexible body wrap has marking indicia to enable an unskilled user to position said body wrap such that said overlapping stimulator coils are properly disposed to enable optimum nerve stimulation.

4. The electromagnetic stimulating device of claim 1, wherein said flexible body wrap is disposable.

5. The electromagnetic stimulating device of claim 1, wherein said plurality of overlapping stimulator coils comprises three overlapping stimulator coils, one center target coil and two flanking coils which can be sequentially or simultaneously electrically energized to create an electromagnetic field near said target coil which is substantially greater than in any single stimulator or flanking coil.

6. A method to electromagnetically stimulate anatomic regions of a patient to prevent and treat medical conditions including: muscular atrophy, musculoskeletal pain, arthritis, urinary incontinence, neuropathic bowel and bladder as well as weight loss, comprising the steps of:

(a) providing an electromagnetic stimulating device having a plurality of overlapping stimulator coils for conducting electrical current;

(b) providing an electrical current means connected to said overlapping stimulator coils so as to be able to independently energize each coil in a predetermined sequence such that each coil will generate its own independent electromagnetic field;

(c) providing an ergonomic flexible body wrap capable of being adjustably and temporarily secured to the body of said patient in which said overlapping stimulator coils are disposed;

(d) stimulating the appropriate body tissues of said patient by sequentially or simultaneously electrically energizing said plurality of overlapping coils in said ergonomic flexible body wrap thereby creating alternating and pulsating electromagnetic fields.

7. An electromagnetic stimulating device comprising:

(a) a plurality of overlapping stimulator coils for conducting electrical current, which are co-planar and are disposed in an ergonomic flexible body wrap capable of being secured to the body of a patient;

(b) an electrical current means connected to said overlapping stimulator coils so as to be able to independently energize each coil in a predetermined sequence such that each coil will generate its own independent electromagnetic field;

whereby, anatomic regions of a patient can be stimulated so as to prevent and treat medical conditions including: muscular atrophy, musculoskeletal pain, arthritis, urinary incontinence, neuropathic bowel and bladder as well as weight loss.

8. The electromagnetic nerve stimulating device of claim 7, wherein said flexible body wrap has marking indicia to enable an unskilled user to position said body wrap such that said overlapping stimulator coils are properly disposed to enable optimum stimulation of the anatomic region.

9. The electromagnetic stimulating device of claim 7, wherein said flexible body wrap is disposable.

10. The electromagnetic stimulating device of claim 7, wherein there are three or more overlapping stimulator coils, one center target coil and two or more flanking coils which can be sequentially or simultaneously electrically energized to create an electromagnetic field near said target coil which is substantially greater than in any one of said stimulator or flanking coil.

* * * * *